United States Patent
Atanasoska et al.

(10) Patent No.: US 7,899,552 B2
(45) Date of Patent: Mar. 1, 2011

(54) CONDUCTIVE COMPOSITE ELECTRODE MATERIAL

(75) Inventors: L. Liliana Atanasoska, Edina, MN (US); J. Lee Shippy, III, Wilmington, NC (US); Tracee E. J. Eidenschink, Wayzata, MN (US); Chandru Chandrasekaran, Mercer Island, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 148 days.

(21) Appl. No.: 12/237,099

(22) Filed: Sep. 24, 2008

(65) Prior Publication Data

US 2009/0099634 A1    Apr. 16, 2009

Related U.S. Application Data

(60) Provisional application No. 60/979,906, filed on Oct. 15, 2007.

(51) Int. Cl.
*A61N 1/05* (2006.01)

(52) U.S. Cl. .......................................................... 607/122

(58) Field of Classification Search ........... 607/115–121
See application file for complete search history.

(56) References Cited

U.S. PATENT DOCUMENTS

| | | | |
|---|---|---|---|
| 2,169,250 | A | 8/1939 | Izard |
| 4,043,331 | A | 8/1977 | Martin et al. |
| 5,187,032 | A | 2/1993 | Sasaki et al. |
| 5,522,879 | A | 6/1996 | Scopelianos |
| 5,529,579 | A | 6/1996 | Alt et al. |
| 5,571,163 | A | 11/1996 | Helland |
| 5,951,597 | A | 9/1999 | Westlund et al. |
| 5,964,794 | A | 10/1999 | Bolz et al. |
| 6,295,474 | B1 | 9/2001 | Munshi |
| 6,718,628 | B2 | 4/2004 | Munshi |
| 6,743,273 | B2 | 6/2004 | Chung et al. |
| 6,856,840 | B2 | 2/2005 | Munshi |
| 6,999,821 | B2 | 2/2006 | Jenney et al. |
| 7,010,358 | B1 | 3/2006 | Kroll et al. |
| 7,689,291 | B2 * | 3/2010 | Polkinghorne et al. ........ 607/115 |
| 2002/0022826 | A1 * | 2/2002 | Reynolds et al. .......... 604/890.1 |

(Continued)

FOREIGN PATENT DOCUMENTS

FR    2696347    4/1994

(Continued)

OTHER PUBLICATIONS

Yu et al., "Production of Submicrometer Diameter Fibers by Two-Fluid Electrospinning," Advanced Materials 16(17): 1562-1566, Sep. 2004.

(Continued)

*Primary Examiner* — Carl H Layno
*Assistant Examiner* — Brian T Gedeon
(74) *Attorney, Agent, or Firm* — Faegre & Benson LLP

(57) ABSTRACT

A medical electrical lead and body implantable electrode suitable for a variety of medical applications are disclosed. In general, the electrode includes a composite material having particles of pseudo-capacitive material, such as iridium oxide, dispersed within a polymer matrix including a polyelectrolyte. The polymer matrix can also include a conductive polymer doped with an excess of the polyelectrolyte. The composite may used to form the electrode itself or an electrode coating. The presence of a pseudo-capacitive material within the composite may increase the charge-storage capacity of the electrode and may allow for safe deliveries of charge densities within an electrochemical window suitable for pacing a patient's heart.

23 Claims, 2 Drawing Sheets

U.S. PATENT DOCUMENTS

| | | |
|---|---|---|
| 2004/0121528 A1 | 6/2004 | Krulevitch et al. |
| 2004/0254513 A1 | 12/2004 | Shang et al. |
| 2005/0107872 A1 | 5/2005 | Mensah et al. |
| 2005/0131509 A1 | 6/2005 | Atanasoska et al. |
| 2005/0175657 A1 | 8/2005 | Hunter et al. |
| 2005/0192665 A1 | 9/2005 | Spenser et al. |
| 2006/0035026 A1 | 2/2006 | Atanasoska et al. |
| 2006/0165952 A1 | 7/2006 | Dubrow |
| 2007/0048452 A1 | 3/2007 | Feng et al. |
| 2007/0060815 A1 | 3/2007 | Martin et al. |
| 2007/0067882 A1 | 3/2007 | Atanasoska et al. |
| 2007/0239245 A1 | 10/2007 | Borgaonkar et al. |
| 2008/0071338 A1 | 3/2008 | Jiang et al. |
| 2008/0071340 A1 | 3/2008 | Atanasoska et al. |
| 2009/0105796 A1 | 4/2009 | Atanasoska et al. |

FOREIGN PATENT DOCUMENTS

| | | |
|---|---|---|
| WO | 9716545 | 5/1997 |
| WO | WO 01/023034 | 4/2001 |
| WO | WO 01/041866 | 6/2001 |
| WO | WO 2004/103470 | 12/2004 |
| WO | WO 2007/130900 | 11/2007 |
| WO | 2008033546 A | 3/2008 |
| WO | 2008036460 A | 3/2008 |
| WO | 2009051945 A | 4/2009 |

OTHER PUBLICATIONS

Berkland et al., Controlling surface nano-structure using flow-limited field-injection electrostatic spraying (FFESS) of poly (D,L-lactide-co-glycolide), Biomaterials 25: 5649-5658, 2004.

Viswanathan et al., "Is Nafion® the only Choice?" Bulletin of the Catalysis Society of India 6: 50-66, 2007.

Hashmi et al., "Investigations on electrochemical supercapacitors using polypyrrole redox electrodes and PMMA based gel electrolytes," European Polymer Journal 41: 1373-1379, 2005.

Liu et al., "Fundamental studies of novel inorganic-organic zwitterionic hybrids. 1. Preparation and characterizations of hybrid zwitterionic polymers," Journal of Non-Crystalline Solids 351: 3050-3059, 2005.

Hashmi et al., "Polypyrrole and poly(3-methyl thiophene)-based solid state redox supercapacitors using ion conducting polymer electrolyte," Solid State Ionics 152-153: 883-889, 2002.

Rajendran et al.,"Characterization of plasticized PMMA-LiBF4 based solid polymer electrolytes," Bull. Mater. Sci. 23 (1): 27-29, Feb. 2000.

Snyder et al., "Polymer eletrolytes and polyelectrolytes: Monte Carlo simulations of thermal effects on conduction," Solid State Ionics 147: 249-257, 2002.

Rikukawa et al., "Proton-conducting polymer electrolyte membranes based on hydrocarbon polymers," Prog. Polym. Sci 25: 1463-1502, 2000.

Huang et al., "Morphology and ionic conductivity of solid polymer electrolytes based on polyurethanes with various topological structures," Journal of Materials Science 39: 1221-1225, 2004.

Mokrini et al., "Proton exchange membranes based on PVDF/SEBS blends," Journal of Power Sources 154: 51-58, 2006.

Inzelt et al., "Electron and proton conducting polymers: recent developments and prospects," Electrochimica Acta 45: 2403-2421, 2000.

Lee et al., "Preparation and ionic conductivity of sulfonated-SEBS/SiO2/plasticizer composite polymer electrolyte for polymer battery," Solid State Ionics 164: 65-72, 2003.

Oh et al., "New Interpenetrating Network-Type Siloxane Polymer Electrolyte," Electrochemical and Solid-State Letters 5(11): E59-E61, 2002.

Zong et al., "Electrospun fine-textured scaffolds for heart tissue constructs," Biomaterials 26: 5330-5338, 2005.

Liu, "Adsorption of bovine serum albumin and fibrinogen on hydrophilicity-controllable surfaces of polypyrrole doped with dodecyl benzene sulfonate-A combined piezoelectric quartz crystal impedance and electrochemical impedance study," Polymer 47: 3372-3381.

Duan et al., "A study of intra-cochlear electrodes and tissue interface by electrochemical impedance methods in vivo," Biomaterials 25: 3813-3828, 2004.

Hwang et al., "Spectroscopic study on sputtered PEDOT—PSS: Role of surface PSS layer," Organic Electronics 7: 387-396, 2006.

Cogan, "Microelectrode coatings for neural stimulation and recording," Proceedings of the 25th Annual International Conference of the IEEE EMBS, Cancun, Mexico, Sep. 17-21, 2003, pp. 3798-3801.

Geddes et al., "Criteria for the Selection of Materials for Implanted Electrodes," Annals of Biomedical Engineering 31:879-890, 2003.

Snaith et al., Morphological and electronic consequences of modifications to the polymer anode 'PEDOTt:PSS,' Polymer 46: 2573-2578, 2005.

Cuentas-Gallegos et al., "Physical and electrochemical characterization of nanostructured composites formed by TiO2 templates and PEDOT-PPS. films," Electrochimica Acta 51: 3794-3801, 2006.

Elizabeth et al., "Preparation and Characterization of PVC/PMMA Blend Polymer Electrolytes Complexed wtih LiN (C2F5S02)2," Polimeros: Ciencia e Tecnologia 14(1): 1-7, 2004.

Huang et al., "Electrochemical and spectroelectrochemical monitoring of supercapacitance and electrochromic properties of hydrous ruthenium oxide embedded poly(3,4-ethylenedioxythiophene)-poly-(styrene sulfonic acid) composite," Electrochimica Acta 51: 3469-3476, 2006.

Sun et al., "Near-Field Electrospinning," NANO Letters 6(4): 839-842, 2006.

Huang et al., "Highly dispersed hydrous ruthenium oxide in poly (3,4-ethylenedioxythiophene)-poly(styrene sulfonic acid) for supercapacitor electrode," Electrochimica Acta 52: 1058-1063.

Dissertation by Salvatore Timpanaro,"Conductive Properties and Morphology of Conjugated Molecular Materials Studied by Local Probe Techniques," Universitat Potsdam, Oct. 2004, 96 pp.

Louwet, "PEDOT/PSS: synthesis, characterization, properties and applications," Synthetic Metals 135-136: 115-117, 2003.

De Giglio, "Electropolymerization of pyrrole on titanium substrates for the future development of new biocompatible surfaces," Biomaterials 22: 2609-2616, 2001.

Shi, "A novel electrically conductive and biodegradable composite made of polypyrrole nanoparticles and polylactide," Biomaterials 25: 2477-2488, 2004.

Vernitskaya, "Polypyrrole: a conducting polymer; its synthesis, properties and applications," Russian Chemical Reviews 66(5): 443-457, 1997.

Song, "Supercapacitive properties of polyaniline/Nafion/hydrous RuO2 composite electrodes," Journal of Power Sources 166: 297-301, 2007.

Murugan et al., "Enhancement of double-layer capacitance behavior and its electrical conductivity in layered poly (3,4-ethylenedioxythiophene)-based nanocomposites," Applied Physics Letters 87: 243511, 2005.

International Search Report and Written Opinion of international application No. PCT/US2008/077522, mailed Dec. 22, 2008, 14 pp.

Invitiation to Pay Additional Fees and, Where Applicable, Protest Fee with Partial International Search issued in PCT/US2008/077527, mailed Jul. 3, 2009, 5 pages.

International Search Report and Written Opinion issued in PCT/US2008/077522, mailed Dec. 22, 2008, 8 pages.

International Search Report and Written Opinion issued in PCT/US2007/067757, mailed Oct. 26, 2007, 11 pages.

Lee, J. L., "Polymer Nanoengineering for Biomedical Applications", Annals of Biomedical Engineering,34(1), (2006), 75-88.

Boland, E. D., et al., "Electrospinning collagen and elastin: preliminary vascular tissue engineering", Front Biosci., 9, (May 1, 2004),1422-32.

Grafe, T. et al., "Polymeric Nanofibers and Nanofiber Webs: A New Class of Nonwovens", INTC 2002: International Nonwovens Technical Conference (Joint INDA—TAPPI Conference), (Sep. 24-26, 2002.),1-13.

Kalluri, R., "Basement membranes: structure, assembly and role in tumour angiogenesis", Nat Rev Cancer., 3(6), (Jun. 2003), 422-33.

Mercier, I. et al., "Interactions of human skin fibroblasts with monomeric or fibrillar collagens induce different organization of the cytoskeleton", Exp Cell Res., 225(2), (Jun. 15, 1996),245-56.

Schindler, M. et al., "A synthetic nanofibrillar matrix promotes in vivo-like organization and morphogenesis for cells in culture", Biomaterials, 26(28), (Oct. 2005),5624-5631.

Schmeichel, K. L. et al., "Modeling tissue-specific signaling and organ function in three dimensions", J Cell Sci., 116(Pt 12), (Jun. 15, 2003),2377-88.

International Search Report and Written Opinion issued in PCT/US2008/077527, mailed Jun. 15, 2010, 20 pages.

* cited by examiner

CONDUCTIVE COMPOSITE ELECTRODE MATERIAL

CROSS-REFERENCE TO RELATED APPLICATION

This application claims the benefit of Provisional Application Ser. No. 60/979,906, filed Oct. 15, 2007, entitled CONDUCTIVE COMPOSITE ELECTRODE MATERIAL, which is herein incorporated by reference in its entirety.

TECHNICAL FIELD

This invention relates to body implantable medical devices, and more particularly, to implantable electrodes for sensing electrical impulses in body tissue or for delivering electrical stimulation pulses to an organ or a nerve.

BACKGROUND

Cardiac pacing leads are well known and widely employed for carrying pulse stimulation signals to the heart from a battery operated pacemaker, or other pulse generating means, as well as for monitoring electrical activity of the heart from a location outside of the body. Electrical energy is applied to the heart via an electrode to return the heart to normal rhythm. Some factors that affect electrode performance include polarization at the electrode/tissue interface, electrode capacitance, sensing impedance, and voltage threshold. In all of these applications, it is highly desirable to optimize electrical performance characteristics at the electrode/tissue interface.

Electrode materials intended for low threshold cardiac pacing or neuro-stimulation are required to have high electrical efficiency and minimal polarization loss during charge injection. The electrode used for electrical stimulation also needs to have high impedance, meaning a small geometrical surface area, in order to prevent premature battery depletion. The small geometric area translates into high current density that can cause the electrode potential to exceed the limits of a safe electrochemical window where no gas evolution or corrosion of the electrode takes place.

Charge injection efficiency is directly related to electrochemically active area and capacitance of the implantable electrode. Electrode capacitance is directly proportional to charge storage capacity ($mC/cm^2$). The presence of a pseudo-capacitive material increases the electrode charged-storage capacity and allows for safe deliveries of charge densities.

SUMMARY

According to one embodiment, the present invention is a medical electrical lead. The medical electrical lead includes a lead body including a conductor extending from a proximal end adapted to be connected to a pulse generator to a distal end. The medical electrical lead also includes at least one electrode. The electrode is operatively connected to the conductor. According to one embodiment, the electrode includes a composite material including a negatively-charged polyelectrolyte and a pseudo-capacitive material. In still further embodiments, the electrode includes a conductive polymer doped with an excess of the negatively charged polyelectrolyte or ionomer.

According to yet another embodiment, the electrode includes a base material operatively connected to the conductor and a coating disposed over at least a portion of the base material. The coating includes the negatively charged polyelectrolyte material and the pseudo-capacitive material.

According to yet another embodiment, the present invention is a body implantable electrode. The body implantable electrode includes a conductive base. The conductive base includes a conductive polymer, a negatively charged polyelectrolyte and a pseudo-capacitive material.

According to another embodiment, the conductive base also includes a conductive metal base and a coating disposed over at least a portion of the conductive base. According to this embodiment, the coating includes the conductive polymer, the negatively charged polyelectrolyte and a pseudo-capacitive material.

According to yet another embodiment, the body implantable electrode includes a conductive base material and a coating including a first layer and a second layer disposed over a least a portion of the conductive base material. The first layer includes a pseudo-capacitive material. The second layer includes a conductive polymer and a negatively charged electrolyte.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
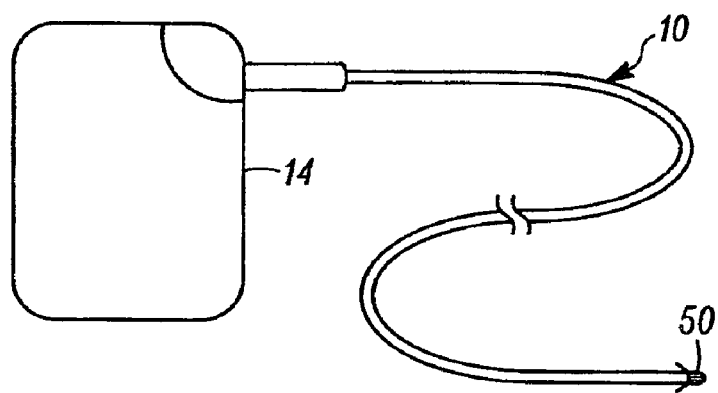
FIG. 1 is a schematic view of a lead and a pulse generator according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

FIG. 1 is a schematic view of a medical electrical lead 10 coupled to a pulse generator 14. In one embodiment, the lead 10 can be adapted to deliver pacing energy to a patient's heart.

Alternatively, the lead 10 can be a adapted for sensing and receiving electrical signals from a patient's heart. In still further embodiments of the present invention, the lead 10 can be adapted for neuro-stimulation applications.

The pulse generator 14 can be implanted in a surgically-formed pocket in a patient's chest or other desired location. The pulse generator 14 generally includes a power supply such as a battery, a capacitor, and other components. Additionally, the pulse generator 14 generally includes electronic components to perform signal analysis, processing, and control. For example, the pulse generator 14 can include microprocessors to provide processing and evaluation to determine and deliver electrical shocks and pulses of different energy levels and timing for ventricular defibrillation, cardioversion, and pacing to a heart in response to cardiac arrhythmia including fibrillation, tachycardia, and bradycardia.

Figure 2:
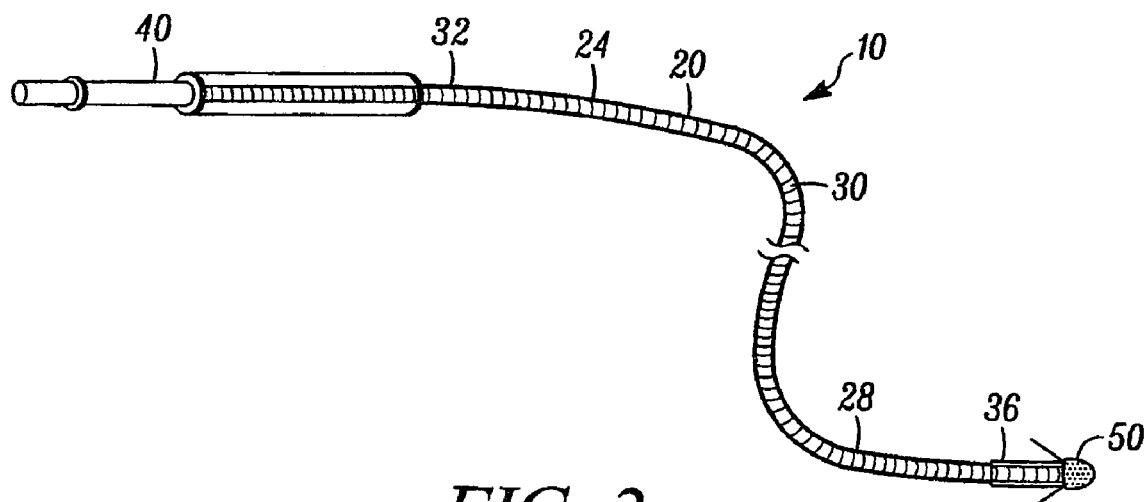
FIG. 2 is a partial cross-sectional view of a lead shown in FIG. 1 according to an embodiment of the present invention.

FIG. 2 is a partial cross-sectional view of the lead 10 shown in FIG. 1. As shown in FIG. 2, the lead 10 includes an elongated, flexible lead body 20 having a proximal portion 24 and a distal portion 28. In one embodiment of the present invention, the lead body 20 includes a lumen for receiving a guiding element such as a guidewire or a stylet.

Cardiac lead 10 also includes one or more conductors 30, such as a coiled conductor, extending from a proximal end 32 to a distal end 36 of the lead body 20. The proximal end 32 is configured to be operatively connected to a pulse generator 14 via a connector 40. Conductor 30 is generally helical in configuration and includes one or more conductive wires or filaments. The conductor 30 is operatively connected to at least one electrode 50 located on the lead body 20. The lead 10 may include a plurality of electrodes as necessary or desired.

Figure 3A:
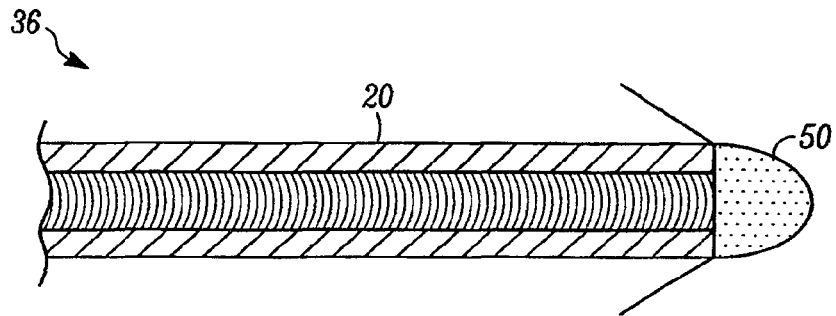
FIG. 3A is a cross-sectional view of a distal portion of a lead according to an embodiment of the present invention.
Figure 3B:
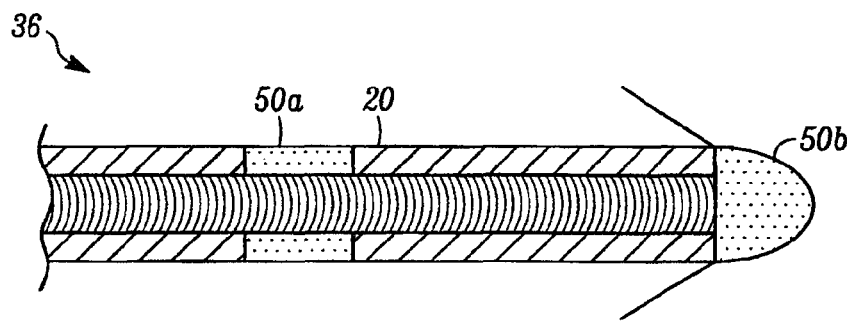
FIG. 3B is a cross-sectional view of a distal portion of a lead according to another embodiment of the present invention.

FIGS. 3A and 3B are partial cross-sectional views of the distal end 36 of the lead body 20 according to various embodiments of the present invention. As shown in FIG. 3A, the electrode 50 is a distal tip electrode 50b located at the distal end 36 of the lead body 20. According to another exemplary embodiment of the present invention, as shown in FIG. 3B, body 20 can include a proximal electrode 50a and/or a distal tip electrode 50b, making the lead 10 a bipolar lead.

In various embodiments, as shown in FIGS. 3A and 3B, the electrode 50 includes a conductive composite material. According to one exemplary embodiment of the present invention, the electrode 50 is formed from a composite including a conductive polymer, a polyelectrolyte, and a pseudo-capacitive material.

According to one embodiment of the present invention, the conductive polymer is an intrinsically conductive polymer. Intrinsically conductive polymers include conjugated polymers and electronically conductive polymers. Intrinsically conductive polymers are conductive without requiring a non-polymeric conductive filler or coating, such as metallic compound or carbon. Intrinsically conductive polymers include alternating single and double bonds forming a conjugated backbone that displays electronic properties. Charge in intrinsically conductive polymers is transported along and between polymer molecules via charge carriers generated along the conjugated backbone.

Intrinsically conductive polymers may include dopants to enhance their conductivity. Dopants may also help to control the conductivity characteristics of the polymer. The conductivity of intrinsically conductive polymers can generally range from semi-conducting to super conducting, depending upon the doping levels. Some intrinsically conductive polymers may also exhibit a quasi-redox behavior that is highly reversible giving them pseudo-capacitive properties. Examples of intrinsically conductive polymers include, but are not limited to, the following: polypyrrole, polyacetylene, polythiophene, polyethylenedioxythiophene, poly(p-phenyl vinylene), polyaniline, polynapthalene, other suitable conductive polymers, and mixtures thereof.

The inclusion of a conductive polymer into the electrode composite may increase its biocompatibility, reduce pacing thresholds, and improve sensing performance. Additionally, the inclusion of a conductive polymer may present an organic interface to biological tissue instead of a metallic interface (e.g. metallic electrode), which may facilitate a favorable biological response to the implant. Inflammatory and healing response of the tissue at the local site may be controlled and/or altered to reduce necrosis in the area next the to the lead and may reduce the thickness of any resultant fibrotic capsule.

Polyelectrolytes (also referred to as a polymer electrolyte or ionomer) are polymers whose units bear an electrolyte group. These groups will dissociate in aqueous solutions, making the polymers charged. Polyelectrolytes can be positively (cationic) or negatively (anionic) charged. Some polyelectrolytes include both cationic and anionic repeating groups. Exemplary negatively charged polyelectrolytes (polyanions) include, but are not limited to, the following: polystyrene sulfonate (PSS), polyglutamic acid, Nafion®, and mixtures thereof. Polyelectrolytes can also include polymer drug conjugates. Exemplary polymer drug conjugates include conjugates of polyglutamate or polyethylene glycol with paclitaxel. Incorporating a polymer drug conjugate into the electrode composite may be a useful way of locally delivering a therapeutic agent to a targeted site within a patient's heart.

A polyelectrolyte can be used to dope a conductive polymer to form a polymer matrix that is both a good ion and electron conductor. Doping a conductive polymer with anions induces an electron conductive path along the conjugated bonds that makes these polymers "metal-like". One such example of a conductive polymer doped with a negatively charged polyelectrolyte includes poly(3,4-ethylenedioxythiophene) doped with an excess of polystyrene sulfonate (PSS), designated as PEDOT-PSS. PEDOT-PSS is a non-stochiometric polyelectrolyte complex of PEDOT having an excess of PSS. Another example of a conductive polymer doped with a negatively-charged polyelectrolyte includes polypyrrole doped with polyglutamic acid. The incorporation of a polyelectrolyte in the electrode composite that allows every volume of the electrode composite to be generally permeable to small molecules, resulting in an extremely high effective electrode surface area. Additionally, the bulk type matrix eliminates the abrupt electrode-tissue interface. The high electrode surface area combined with the elimination of the abrupt electrode-tissue interface allows for more efficient charge transfer process.

According to one embodiment of the present invention, the electrode composite also includes a pseudo-capacitive material. A pseudo-capacitive material is a material that is capable of undergoing a reversible faradaic process, such as an oxidation/reduction (redox) reaction. Pseudo-capacitors are capable of storing large amounts of charge, and can serve as high or ultra-high capacitors. When the capacitance of a material is measured using cyclic voltammetry, capacitance is directly proportional to the measured current. Some conductive polymers such as polyaniline and polythiophenes can also behave as pseudo-capacitors. According to one embodiment of the present invention, the pseudo-capacitive material is dispersed throughout the conductive polymer/polymer electrolyte matrix. Exemplary pseudo-capacitive materials include, but are not limited to, transition metal oxides such as iridium oxide, ruthenium oxide, rhodium oxide, osmium oxide, titanium oxide, and combinations thereof. The incorporation of one or more of these materials into a conductive polymer or a conductive polymer doped with a polyelectrolyte may further boost the capacitance properties of the pseudo-capacitive materials. The pseudo-capacitive material is dispersed throughout the polymer matrix in the form or microparticles or nanoparticles. In some embodiments, the dispersion of pseudo-capacitive particles can be a uniform dispersion of particles.

The amount of pseudo-capacitive material present in the conductive composite material is important for maintaining the electrode potential within a safe electrochemical window for pacing. The amount of pseudo-capacitive material present in the electrode composite should be sufficient to maintain the electrode potential within a safe electrochemical window for pacing. A safe electrochemical window for pacing can be defined as the potential range within which only reversible reactions occur. This can also be referred to as the charge injection limit. In general, the potential limits of the electrochemical window for pacing are the hydrolysis of water to oxygen and protons (anodic limit) and of hydrogen to hydroxide ions (cathodic limit) which is approximately 2V. Within this potential range a number of additional reactions may also occur.

|   | reduction | E°/volts |
|---|---|---|
| 1 | O2 + 4H+ + 4e− ® 2H2O | +1.229 |
| 2 | Ag+ + e− ® Ag | +0.7996 |
| 3 | Cu2+ + 2 e− ® Cu | +0.3419 |
| 4 | Fe2+ + 2 e− ® Fe | −0.447 |
| 5 | Zn2+ + 2 e− ® Zn | −0.7628 |
| 6 | 2H2O + 2 e− ® H2 + 2OH— | −0.83 |

The voltage drop values at the electrode tissue interface remain within the cathodic and anodic potential limits of the hydrolysis of water resulting in high capacitance of the electrode.

According to an embodiment of the present invention, the amount of pseudo-capacitive material present in the conductive electrode composite material should be sufficient to maintain the electrode potential within an electrochemical window of about 2 V. According to a further embodiment of the present invention, the conductive electrode composite material includes a pseudo-capacitive material present in an amount no greater than about 35 wt % of the total weight of the fibrous matrix.

According to one embodiment of the present invention, the electrode is formed from a composite including poly(3,4-ethylenedioxythiophene) (PEDOT) doped with an excess of polystyrene sulfonate (PSS) and iridium oxide. The iridium oxide is dispersed through out the polymer matrix in the form of microparticles or nanoparticles. In a further embodiment of the present invention the iridium oxide is uniformly dispersed throughout the polymer matrix.

According to another further embodiment of the present invention, the electrode is formed from a composite including polypyrrole doped with an excess of polyglutamic acid and iridium oxide.

Figure 4:
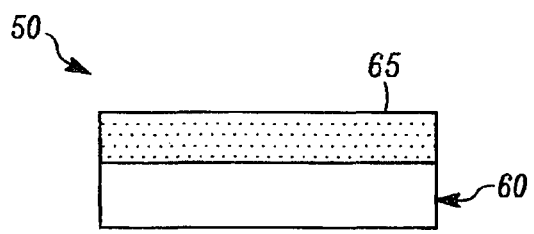
FIG. 4 is a side, cross-sectional view of an electrode according to an embodiment of the present invention.

FIG. 4 is a side, cross-sectional view of an electrode 50 according to another embodiment of the present invention. As shown in FIG. 4, the electrode 50 includes a conductive base material 60 and a coating 65 comprising a conductive composite material disposed on the base material. The base material can be formed from platinum, stainless steel, MP35N, a platinum-iridium alloy or another similar conductive material. The coating 65 is disposed on at least a portion of the conductive base material 60. According to another embodiment of the present invention, the coating 65 covers substantially all an outer surface of the base material.

Figure 5:
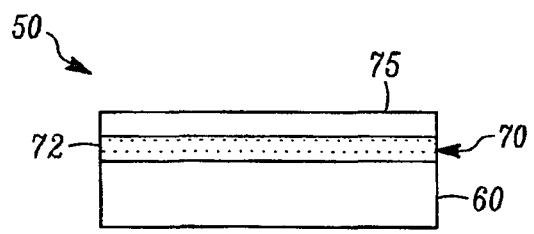
FIG. 5 is a side, cross-sectional view of an electrode according to another embodiment of the present invention.

FIG. 5 is cross-sectional schematic view of an electrode 50 according to yet another embodiment of the present invention. According to this embodiment, the electrode 50 includes a conductive base material 60, a composite coating 70 disposed on at least a portion of the conductive base material 60. The conductive base material 60 can be formed from platinum, stainless steel, MP35N, a platinum-iridium alloy or another similar conductive material.

As shown in FIG. 5, the composite coating 70 includes a first layer 72 and a second layer 75. The first layer 72 is a pseudo-capacitive coating such as those now employed in current lead technology. According to one embodiment, the first layer 72 may have a micro-porous or nano-porous structure. Exemplary materials for forming the first pseudo-capacitive layer on the conductive base material 60 include the transition metal oxides and other capacitive materials some examples of which include, but are not limited to, the following: iridium oxide, ruthenium oxide, rhodium oxide, osmium oxide, titanium oxide, platinum iridium, platinized platinum, iridium oxide, titanium nitride, titanium oxynitride, titanium carbide, tantalum oxide, tantalum nitride, tantalum oxynitride, and combinations thereof.

A polymer matrix including conductive polymer doped with an excess of a negatively-charged polyelectrolyte forms the second layer 75. The second layer 75 of the composite coating 70 is disposed on at least a portion of the first layer 72. According to another embodiment, the second layer 75 is disposed over substantially all of the first layer 72. The presence of the conductive polymer/polyelectrolyte matrix may increase the capacitive properties of the first layer 72. According to one embodiment, the conductive polymer/polyelectrolyte matrix includes poly(3,4-ethylenedioxythiophene) (PEDOT) doped with an excess of polystyrene sulfonate (PSS). According to another embodiment of the present invention, the conductive polymer/polyelectrolyte matrix includes polypyrrole doped with an excess of polyglutamic acid. Still other combinations of a conductive polymer doped with an excess of a negatively charged polyelectrolyte are possible. In yet other embodiments of the present invention, the second layer 75 includes a conductive polymer doped with an excess of a negatively-charged polyelectrolyte and a pseudo-capacitive material such as described above.

According to various embodiments of the present invention, the electrode 50 and/or coatings 65 and 70 may be formed by dip-coating, brush-coating, drop coating, electrospray coating, electrochemical deposition, electrospinning, sputtering, or by electrodeposition. In further embodiments, the coatings 65 and 70 may be coated on the surface of the electrode 50 by chemical deposition, plasma coating, or bipolar electrode position. These and other methods are well known to those of skilled in the art.

In one embodiment of the present invention, conductive polymers such as polypyrrole or PEDOT can be formed by passing a current through a conductive substrate while the substrate is immersed in an aqueous solution of the monomer. The conductive polymer may incorporate other molecules or dopants that are present in the solution during its formation (e.g., therapeutic agents or biomolecules promoting attachment to tissue).

According to another embodiment, the electrode and or electrode coating may be formed by spray coating. Spray coating may allow for greater control of coating placement which may allow for selectively coating one area of the lead and/or electrode without contaminating other areas of the lead and/or electrode with the spray solution/mixture. Other benefits of spray coating may include decreased waste of coating solution/mixture and uniform coating on the device (e.g., along a lead body or on an electrode).

According to yet another embodiment of the present invention, the electrode composite and/or electrode coating can be formed by spin coating the conductive polymer/polyelectrolyte matrix onto a conductive substrate. Then, cathodic electro-deposition can be used to incorporate or embed particles of the pseudo-capacitive material into the conductive polymer/polyelectrolyte matrix.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical electrical lead comprising:
   a lead body including a conductor extending from a proximal end adapted to be connected to a pulse generator to a distal end; and
   at least one electrode operatively connected to the conductor, the electrode comprising a polymer matrix including a conductive polymer doped with an excess of a negatively charged polyelectrolyte and pseudo-capacitive, transition metal oxide particles dispersed throughout the polymer matrix.

2. The medical electrical lead of claim 1, wherein the electrode includes a conductive base material operatively connected to the conductor and wherein a coating including the polymer matrix is coated over at least a portion of the base material.

3. The medical electrical lead of claim 1, wherein the conductive polymer is selected from the group consisting of polypyrrole, polyaniline, polyacetylene, polythiophene, polyethylenedioxythiophene, poly (p-phenyl vinylene), and mixtures thereof.

4. The medical electrical lead of claim 1, wherein the conductive polymer comprises polyethylenedioxythiophene.

5. The medical electrical lead of claim 1, wherein the negatively charged polyelectrolyte is selected from the group consisting of polystyrene sulfonate, polyglutamic acid, Nafion, and mixtures thereof.

6. The medical electrical lead of claim 1, wherein the negatively charged polyelectrolyte comprises polystyrene sulfonate.

7. The medical electrical lead of claim 1, wherein the pseudo-capacitive, transition metal oxide particles are selected from the group consisting of iridium oxide particles, ruthenium oxide particles, rhodium oxide particles, osmium oxide particles, titanium oxide particles, and combinations thereof.

8. The medical electrical lead of claim 1, wherein the pseudo-capacitive, transition metal oxide particles comprise iridium oxide particles.

9. The medical electrical lead of claim 1 wherein the pseudo-capacitive material is present in a sufficient amount such that an electrode potential of the electrode is maintained within an electrochemical window suitable for pacing a heart.

10. The medical electrical lead of claim 1, wherein the conductive polymer comprises polyethylenedioxythiophene, the negatively charged electrolyte comprises polystyrene sulfonate, and the pseudo capacitive material comprises iridium oxide particles.

11. The medical electrical lead of claim 1, wherein the conductive polymer comprises polypyrrole and the negatively charged electrolyte comprises polyglutamic acid.

12. A medical electrical lead comprising
    a lead body including a conductor extending from a proximal end adapted to be connected to a pulse generator to a distal end; and
    an electrode comprising a conductive base material and a coating comprising a conductive composite material disposed on at least a portion of the base material, the composite material comprising a polymer matrix comprising a conductive polymer doped with an excess of a negatively charged polyelectrolyte and pseudo-capacitive, transition metal oxide particles dispersed throughout the polymer matrix.

13. The medical electrical lead according to claim 12, wherein the conductive polymer is selected from the group consisting of polypyrrole, polyaniline, polyacetylene, polythiophene, polyethylenedioxythiophene, poly(p-phenyl vinylene), and mixtures thereof.

14. The medical electrical lead of claim 12, wherein the conductive polymer comprises polyethylenedioxythiophene and the negatively charged electrolyte comprises polystyrene sulfonate.

15. The medical electrical lead of claim 12, wherein the negatively charged polyelectrolyte is selected from the group consisting of polystyrene sulfonate, polyglutamic acid, Nafion, and mixtures thereof.

16. The medical electrical lead of claim 12, wherein the negatively charged polyelectrolyte is polystyrene sulfonate.

17. The medical electrical lead of claim 12, wherein the pseudo-capacitive, transition metal oxide particles are selected from the group consisting of iridium oxide particles, ruthenium oxide particles, rhodium oxide particles, titanium oxide particles, osmium oxide particles, and combinations thereof.

18. The medical electrical lead of claim 12, wherein the pseudo-capacitive, transition metal oxide particles comprise iridium oxide particles.

19. The medical electrical lead of claim 12, wherein the conductive polymer comprises polypyrrole and the negatively charged electrolyte comprises polyglutamic acid.

20. A body implantable electrode comprising:
    a conductive metal base;
    a composite coating disposed over at least a portion of the conductive base, composite coating including a polymer matrix comprising a conductive polymer doped with an excess of a negatively-charged polyelectrolyte and pseudo-capacitive, transition metal oxide particles dispersed throughout the polymer matrix.

21. The body implantable electrode of claim 20, wherein the conductive metal base includes a first layer comprising a pseudo-capacitive material and a second layer comprising the composite coating.

22. The body implantable electrode of claim 20, wherein the polymer matrix comprises polyethylenedioxythiophene doped with an excess of polystyrene sulfonate and the pseudo capacitive material comprises iridium oxide particles.

23. The body implantable electrode of claim 20, wherein the polymer matrix comprises polypyrrole doped with an excess of polyglutamic acid.

* * * * *